(12) United States Patent
Inoue et al.

(10) Patent No.: US 11,448,779 B2
(45) Date of Patent: Sep. 20, 2022

(54) RADIOLOGICAL IMAGING APPARATUS, MANUFACTURING METHOD OF THE SAME, AND IMAGING SYSTEM

(71) Applicant: CANON KABUSHIKI KAISHA, Tokyo (JP)

(72) Inventors: Masato Inoue, Toda (JP); Shoshiro Saruta, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 40 days.

(21) Appl. No.: 16/457,496

(22) Filed: Jun. 28, 2019

(65) Prior Publication Data

US 2019/0324159 A1 Oct. 24, 2019

Related U.S. Application Data

(63) Continuation of application No. PCT/JP2017/045808, filed on Dec. 20, 2017.

(30) Foreign Application Priority Data

Jan. 16, 2017 (JP) .............................. JP2017-005269

(51) Int. Cl.
*G01T 1/20* (2006.01)
*G01T 1/29* (2006.01)

(52) U.S. Cl.
CPC .......... *G01T 1/2018* (2013.01); *G01T 1/2914* (2013.01)

(58) Field of Classification Search
None
See application file for complete search history.

(56) References Cited

U.S. PATENT DOCUMENTS

| | | | |
|---|---|---|---|
| 2008/0011960 A1* | 1/2008 | Yorkston | G21K 4/00 250/370.09 |
| 2008/0292057 A1 | 11/2008 | Finkler | |
| 2010/0104067 A1 | 4/2010 | Okada | |
| 2012/0205543 A1 | 8/2012 | Nakatsugawa | |

(Continued)

FOREIGN PATENT DOCUMENTS

| | | |
|---|---|---|
| JP | 2007-38013 A | 2/2007 |
| JP | 2010-101805 A | 5/2010 |

(Continued)

OTHER PUBLICATIONS

Wikipedia article, "Elastic modulus" retrieved from en.wikipedia.org/wiki/Elastic_modulus on Dec. 15, 2021.*

*Primary Examiner* — Edwin C Gunberg
(74) *Attorney, Agent, or Firm* — Canon U.S.A., Inc. IP Division

(57) ABSTRACT

A radiological imaging apparatus includes a first panel where a plurality of radiation detecting elements are arrayed on a first substrate, a second panel where a plurality of radiation detecting elements are arrayed on a second substrate, and a sheet-shaped adhesion part configured to adhere a second-panel side face of the first panel and a first-panel side face of the second panel to each other, so that the first panel and the second panel are overlaid on each other in planar view as to an upper face of the first substrate. The adhesion part is configured to maintain adhesion of the first panel and the second panel, while tolerating change in relative positions thereof in a planar direction parallel to the upper face of the first substrate.

19 Claims, 6 Drawing Sheets

(56) References Cited

U.S. PATENT DOCUMENTS

| | | |
|---|---|---|
| 2014/0034837 A1 | 2/2014 | Takeda |
| 2018/0052240 A1 | 2/2018 | Tanabe |
| 2018/0126706 A1* | 5/2018 | Erdogan-Haug ......... B32B 1/00 |

FOREIGN PATENT DOCUMENTS

| | | |
|---|---|---|
| JP | 2012-168010 A | 9/2012 |
| JP | 2014-32124 A | 2/2014 |
| JP | 2014-85223 A | 5/2014 |
| JP | 2014-195481 A | 10/2014 |
| WO | 2016/143401 A1 | 9/2019 |

* cited by examiner

RADIOLOGICAL IMAGING APPARATUS, MANUFACTURING METHOD OF THE SAME, AND IMAGING SYSTEM

CROSS-REFERENCE TO RELATED APPLICATIONS

This application is a Continuation of International Patent Application No. PCT/JP2017/045808, filed Dec. 20, 2017, which claims the benefit of Japanese Patent Application No. 2017-005269, filed Jan. 16, 2017, both of which are hereby incorporated by reference herein in their entirety.

TECHNICAL FIELD

The present invention relates to a radiological imaging apparatus, a manufacturing method of the same, and an imaging system.

BACKGROUND ART

There are radiological imaging apparatuses that enable processing of acquiring two sets of image data regarding the same subject, and forming one radiological image based on the difference between these. Specifically, two sets of image data are acquired under amounts of radiation that differ from each other, and the difference thereof is obtained using a predetermined coefficient, thereby observing a desired object site, or the object of observation can be changed (e.g., from organ to bone) by chancing the coefficient. Such processing is called energy subtraction or the like.

PTL 1 describes the structure of a radiological imaging apparatus where two sensor panels are disposed parallel to each other. According to PTL 1, two sets of image data can be acquired at one time by this structure.

CITATION LIST

Patent Literature

PTL 1 Japanese Patent Laid-Open No. 2010-101805

Now, in a case of disposing members between the two sensor panels mentioned above for linking to each other, there is a possibility of damaging one or both of the sensor panels by vibrations, shock, or the like, at the time of handling the radiological imaging apparatus. Specifically, there is a possibility of positional deviation occurring in the planar direction between the two sensor panels due to the aforementioned vibrations, shock, or the like, for example. Accordingly, there are cases where detachment occurs between one or both of the sensor panels and linking portions, and consequently, there are cases where abrasion marks are formed on the surface of the sensor panels. These can lead to lower reliability of the radiological imaging apparatus and lower quality of radiological images.

Note that PTL 1 describes disposing a filter for absorbing part of the radiation between two sensor panels, but does not take into consideration positional deviation occurring between the two sensor panels due to the aforementioned vibrations, shock, or the like.

The present invention provides a technology that advantageous in improvement of reliability of a radiological imaging apparatus that has two sensor panels, and improvement of quality of radiological images.

SUMMARY OF INVENTION

An aspect of the present invention relates to a radiological imaging apparatus, the radiological imaging apparatus including a first panel where multiple radiation detecting elements are arrayed on a first substrate, a second panel where multiple radiation detecting elements are arrayed on a second substrate, and a sheet-shaped adhesion part configured to adhere a second-panel side face of the first panel and a first-panel side face of the second panel to each other, so that the first panel and the second panel are overlaid on each other in planar view as to an upper face of the first substrate. The adhesion part is configured to maintain adhesion of the first panel and the second panel, while tolerating change in relative positions thereof in a planar direction parallel to the upper face of the first substrate.

Further features of the present invention will become apparent from the following description of exemplary embodiments with reference to the attached drawings.

DESCRIPTION OF EMBODIMENTS

Figure 1:
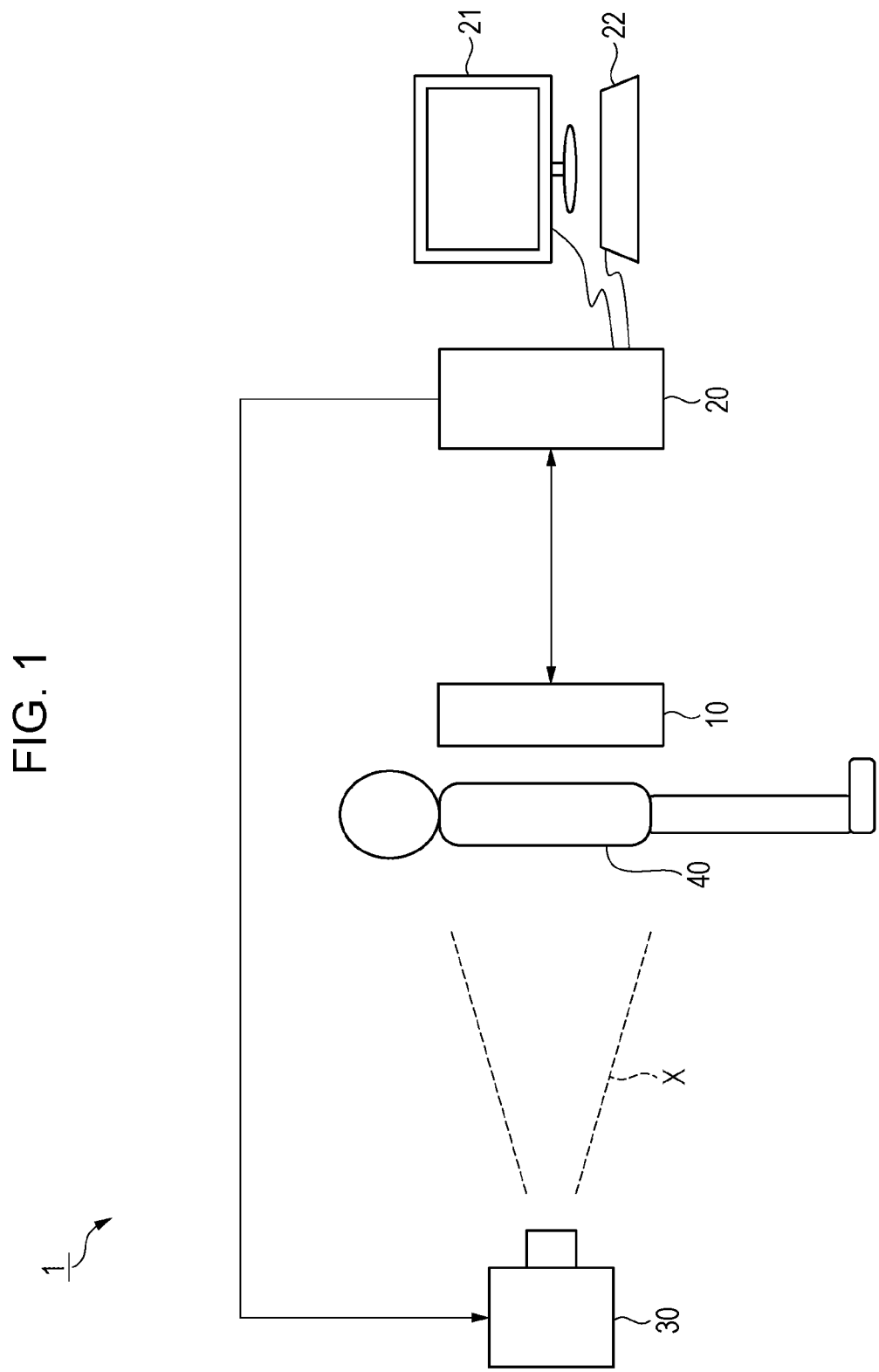
FIG. 1 is a diagram for describing a configuration example of an imaging system.

A preferred embodiment of the present invention will be described below with reference to the attached drawings. Note that the drawings are schematic diagrams compiled to describe structures and configurations, and do not necessarily reflect actual dimensions of the illustrated members. Members that are the same and components that are the same in the drawings are denoted by the same reference numerals, and description of repetitive contents will be omitted below.

FIG. 1 illustrates the configuration of an imaging system 1, of which a radiological examination apparatus or the like is representative. The imaging system 1 includes a radiological imaging apparatus 10, a processor 20, and a radiation source 30. The radiological imaging apparatus 10, which will be described in detail later, detects radiation that has been emitted from the radiation source 30 and passed through a subject 40 such as a patient or the like, and generates image data. Although X-rays are used for the radiation in the present embodiment, alpha rays, beta rays, or the like may be used.

The processor 20 performs predetermined computation processing on a group of signals making up the image data obtained from the radiological imaging apparatus 10. The processor 20 is connected to a display 21 and an input terminal 22. A user, such as a physician or the like, can input information necessary for shooting, such as a site to be examined, irradiation time of radiation, intensity of radiation, and so forth, to the processor 20, using the display 21 and input terminal 22. The processor 20 also displays a radiological image on the display 21 based on image data from the radiological imaging apparatus 10. The user can perform diagnosis based on this radiological image.

The processor 20 in the present embodiment is a personal computer including memory to which a predetermined program is loaded, and a CPU (central processing unit) to execute the same, but in another embodiment may be a computing device having a dedicated integrated circuit (e.g., an ASIC). In other words, it is sufficient for the functions of the processor 20 to be realized by hardware and/or software. The display 21 is a liquid crystal display in the present embodiment, but another known image display device may be used, instead of or in addition to this. The input terminal 22 is a keyboard for a personal computer in the present embodiment, but another known input device may be used, instead of or in addition to this.

Figure 2:
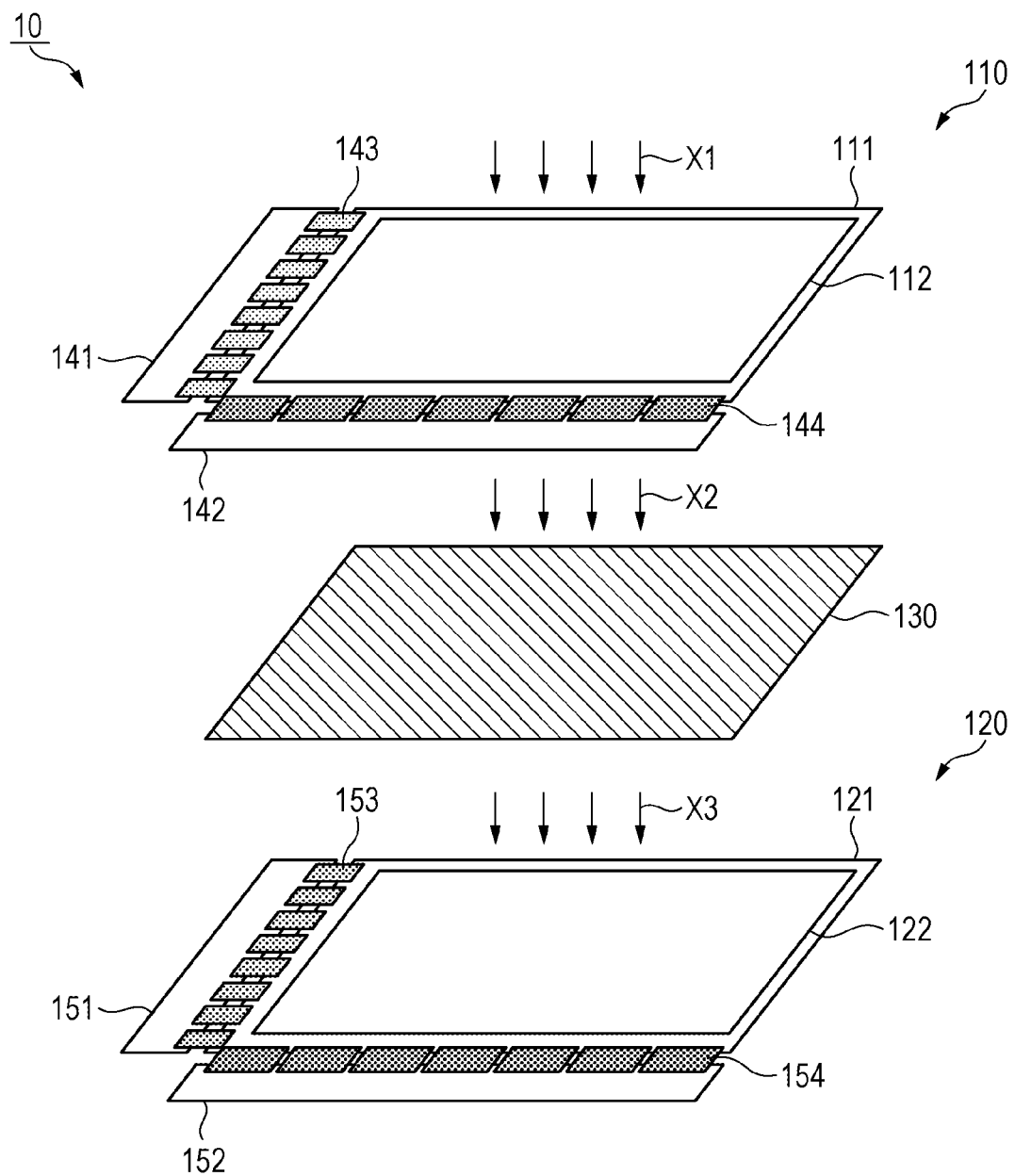
FIG. 2 is a diagram for describing a configuration example of a radiological imaging apparatus.

FIG. 2 illustrates the configuration of the radiological imaging apparatus 10. The radiological imaging apparatus 10 has two sensor panels 110 and 120, and an adhesion part 130 disposed therebetween. In the drawing, the upper side is the radiation source 30 side (radiation emission side). The sensor panel 110 is disposed above the sensor panel 120 in the present embodiment, but the positions may be reversed.

The sensor panel 110 has a substrate 111, and a sensor array 112 formed on the substrate 111. The sensor panel 110 in the present embodiment is a panel that performs radiological imaging by indirect conversion (a method where radiation is converted into light, and the light is converted into electric signals, to detect the radiation). Accordingly, the sensor panel 110 further has a scintillator arrayed to cover the sensor array 112 on the substrate 111, which will be described later in detail. Note that while the embodiment will be described below with reference to the configuration of an indirect conversion arrangement, the contents thereof are applicable to the configuration of a direct conversion arrangement (a method where radiation is directly converted into electric signals) as well.

A glass substrate is used for the substrate 111 in the present embodiment, but a substrate configured of another known insulating material may be used as another embodiment. The sensor array 112 includes multiple radiation detecting elements arrayed on the substrate 111, to form multiple rows and multiple columns. PIN sensors configured of amorphous silicon are used for the radiation detecting elements in the present embodiment, but other sensors (photoelectric converters) for detecting radiation, such as MIS sensors and so forth, may be used.

Each radiation detecting element is connected to a thin-film transistor that is a switching device for reading out signals in accordance with radiation, these making up a single pixel, although detailed description thereof will be omitted here. From this perspective, the sensor array may be referred to as a pixel array.

The sensor panel 120 has the same configuration as the sensor panel 110, and includes a substrate 121 corresponding to the substrate 111, and a sensor array 122 corresponding to the sensor array 112.

The adhesion part 130 is interposed between the sensor panel 110 and sensor panel 120 and adheres these to each other. The adhesion part 130 has radiation absorbency and also elasticity, which will be described in detail later. Alternatively, the adhesion part 130 may have radiation absorbency and also viscoelasticity. The adhesion part 130 is a sheet-shaped member that adheres the face of the sensor panel 110 toward the sensor panel 120 side and the face of the sensor panel 120 toward the sensor panel 110 side to each other (facial adhesion)

The radiological imaging apparatus 10 further has a driving unit 141, a reading unit 142, wiring portions 143 and 144, a driving unit 151, a reading unit 152, and wiring portions 153 and 154. The driving unit 141 is connected to the sensor panel 110 via the wiring portion 143, and can drive or control the sensor array 112. The driving unit 141 according to the present embodiment is configured including a vertical scan circuit, decoder, and so forth. The reading unit 142 is connected to the sensor panel 110 via the wiring portion 144, and can read image data from the sensor array 112. The reading unit 142 according to the present embodiment is configured including a signal amplifier, sampling circuit, horizontal scan circuit, analog-to-digital converter, and so forth.

The driving unit 151, reading unit 152, and wiring portions 153 and 154 corresponding to the sensor panel 120 are also the same as the driving unit 141, reading unit 142, and wiring portions 143 and 144, respectively. That is to say, functions and operations of the driving unit 151, reading unit 152, and wiring portions 153 and 154 correspond to the functions and operations of the driving unit 141, reading unit 142, and wiring portions 143 and 144.

Note that the wiring portions 143 and 153 in the present embodiment are COF (Chip On Film), and may have part of the functions of the driving units 141 and 151, respectively. In the same way, the wiring portions 144 and 154 are COF, and may have part of the functions of the reading units 142 and 152, respectively.

Radiation X1 that has been generated from the radiation source 30 and that has passed through the subject 40 enters the sensor panel 110, and is detected by the sensor array 112, as illustrated in the drawing. Image data is read out from the sensor panel 110 based on the radiation X1 detected by the sensor array 112, by the driving unit 141 and reading unit 142. Thereafter, radiation X2 that has passed through the sensor panel 110 passes through the adhesion part 130, at which time part of the energy is absorbed by the adhesion part 130. Further, following this, radiation X3 that has passed through the adhesion part 130 enters the sensor panel 120, and is detected by the sensor array 122. Image data is read out from the sensor panel 120, by the driving unit 151 and reading unit 152, based on the radiation X3 detected by the sensor array 122.

It is sufficient for the driving sequence by the driving unit 141 (or 151) and the reading sequence by the reading unit 142 (or 152) for reading image data from the sensor panel 110 (or 120) to follow known arrangements, although description will be omitted in the present specification. For example, the driving unit 141 drives the sensor array 112 in increments of rows to output signals, and the reading unit 142 reads signals from the sensor array 112 row by row, and generates image data.

According to the above-described configuration, two sets of image data can be obtained at once from a single radiation shooting, from the sensor panels 110 and 120. At this time, the amount of radiation (intensity) entering the sensor panel 120 is smaller than the amount of radiation entering the sensor panel 110, since part of the radiation energy is absorbed at the adhesion part 130. Accordingly, while the image data obtained from the sensor panel 110 and the image data obtained from the sensor panel 120 both show image information regarding the same subject, there is difference in data values (signals values) therebetween. Energy subtraction processing can then be performed using these two sets of image data. Specifically, a site that is the object of examination can be observed by subjecting these two sets of image data to computation processing using a predetermined coefficient, and the object of observation can be changed to a different site by changing this coefficient.

Figure 3A:
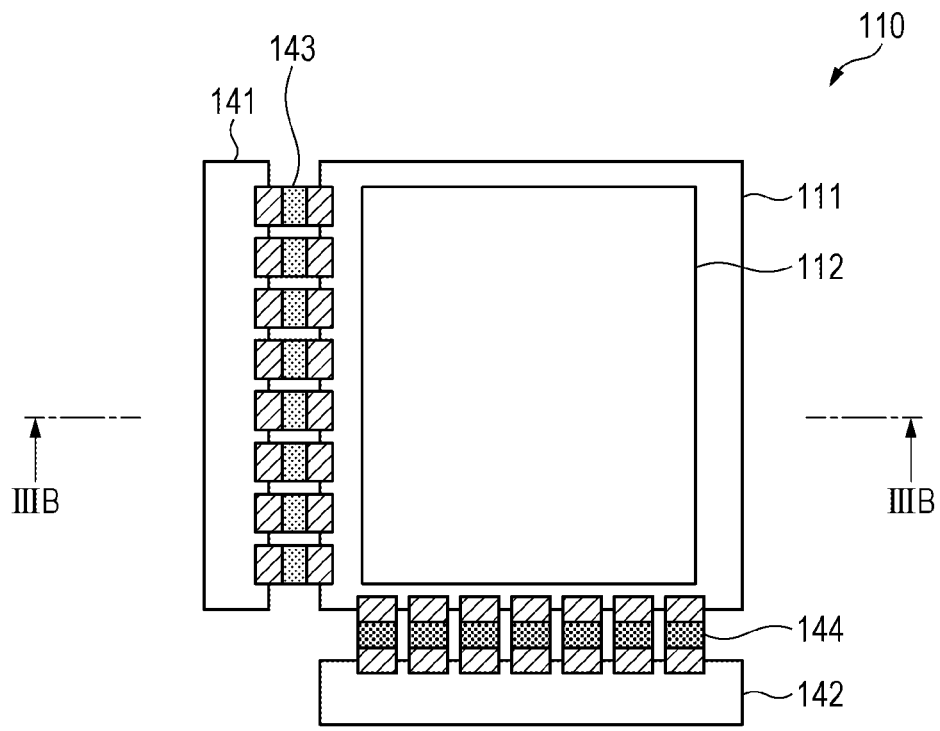
FIG. 3A is a diagram for describing a configuration example of a single sensor panel.
Figure 3B:
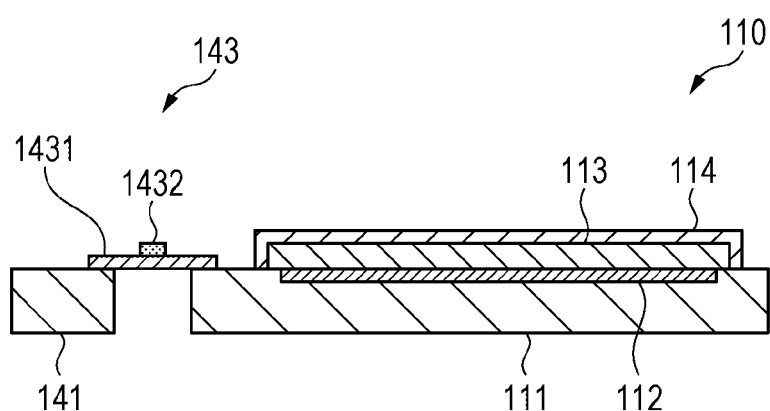
FIG. 3B is a diagram for describing a configuration example of a single sensor panel.

FIG. 3A illustrates a layout of the sensor panel 110 in planar view (Planar view as to the upper face of the substrate 111. Hereinafter referred to simply as "planar view".). FIG. 3B illustrates a cross-sectional structure taken along section line IIIB-IIIB. The sensor panel 110 will be described here, but this is the same for the sensor panel 120 as well.

The sensor panel 110 further has a scintillator 113 disposed so as to cover the sensor array 112 on the substrate 111, and a protective film 114 for preventing deliquescence of the scintillator 113. Thallium-doped cesium iodide is used for the scintillator 113 in the present embodiment, but another known scintillator that emits light under radiation may be used. A material that has humidity preventing properties and also light reflecting properties is used for the protective film 114, such as aluminum or the like for example.

The wiring portion 143 includes a flexible film 1431, and a chip 1432 mounted thereupon, and has a part of the functions of driving the sensor array 112, as described above. Although the wiring portion 143 has been illustrated here in a state extending in parallel to the sensor panel 110 for the sake of description, the wiring portion 143 may be bent at the time of accommodation in housing of the radiological imaging apparatus 10 along with the sensor panel 110 and driving unit 141. The same is true for the other wiring portions 144, 153, and 154.

Figure 4A:
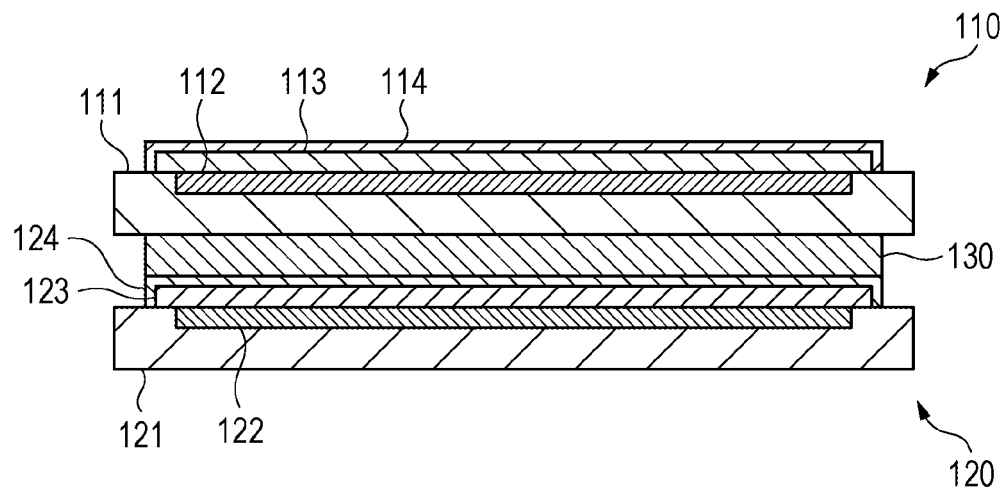
FIG. 4A is a diagram for describing a configuration example of an adhesion part.

FIG. 4A illustrates a form of adhesion of the sensor panels 110 and 120 by the adhesion part 130. Note that the driving unit 141 and so forth are omitted from illustration here, to facilitate viewing of the drawing. The sensor panels 110 and 120 are adhered to each other by the adhesion part 130, so as to both have front-side irradiation configurations in the present embodiment. Specifically, the substrate 111 and a scintillator 123 are positioned between the scintillator 113 and substrate 121, with the adhesion part 130 adhering the lower face of the substrate 111 and the upper face of a protective film 124.

Now, the user generally loads the radiological imaging apparatus 10 on a wagon or the like and transports into an examination room, or carries the radiological imaging apparatus 10 to transport in a case where it is a portable type. Accordingly, there is a possibility that the radiological imaging apparatus 10 will be subjected to vibration or shock or the like at this time, and that the sensor panel 110 and/or sensor panel 120 may peel away from the adhesion part 130, and positional deviation or the like will occur between the sensor panels 110 and 120.

Figure 4B:
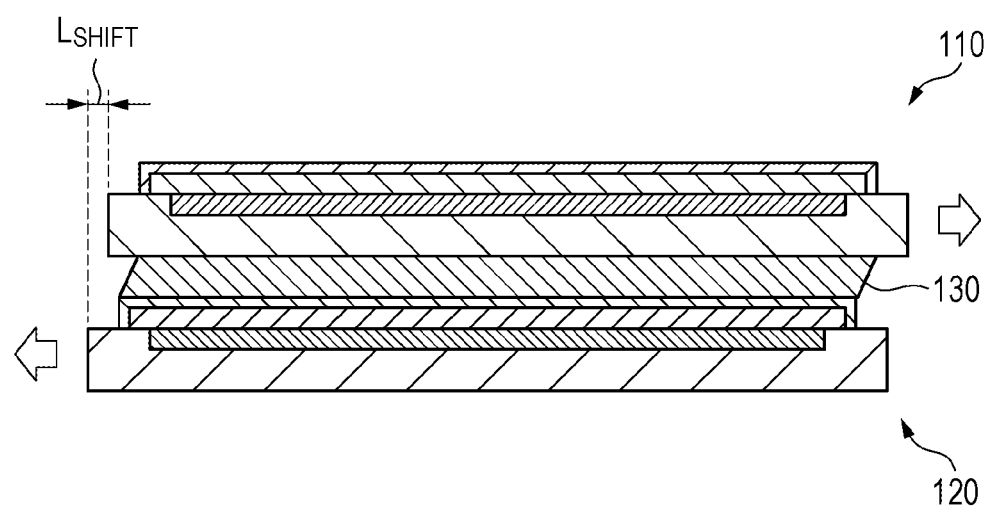
FIG. 4B is a diagram for describing a configuration example of an adhesion part.

Accordingly, the adhesion part 130 is configured to maintain adhesion of the sensor panels 110 and 120, while tolerating change in relative positions of the sensor panel 110 and the sensor panel 120 in a planar direction, as illustrated in FIG. 4B. The planar direction of the sensor panel 110 (or 120) is a direction parallel to the upper face of the substrate 111 (or 121) here. The drawing illustrates a state where the sensor panels 110 and 120 have respectively shifted as to each other in the directions indicated by arrows, by a distance $L_{SHIFT}$ in the planar direction. According to this configuration, adhesion between the sensor panels 110 and 120 can be maintained while suppressing peeling of the adhesion part 130 and positional deviation and the like thereof, and thereby the reliability of the radiological imaging apparatus 10 can be improved and quality of radiological images can be improved.

The following is description of several configuration examples of the adhesion part 130 (referred to as adhesion parts 130A through 130D, respectively, for the sake of distinction), with reference to FIGS. 5A through 5D.

Figure 5A:
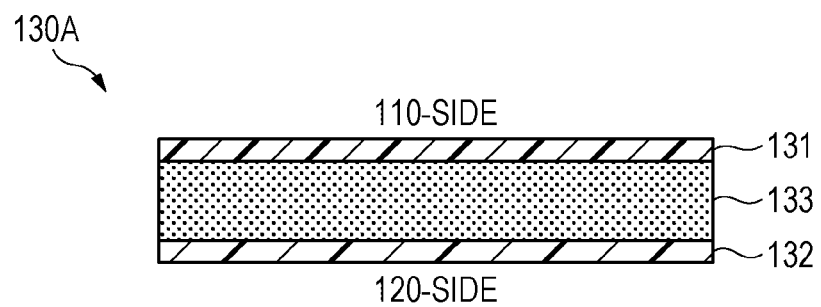
FIG. 5A is a diagram for describing a configuration example of an adhesion part.

FIG. 5A illustrates the configuration of the adhesion part 130A. The adhesion part 130A has a portion 131 at the sensor panel 110 side or near the boundary thereof, a portion 132 at the sensor panel 120 side or near the boundary thereof, and a portion 133 between the portion 131 and portion 132. The portions 131 and 132 are configured having a smaller elastic modulus than the elastic modulus of the portion 133, and the portions 131 and 132 deform more readily than the portion 133 under application of force. On the other hand, the portion 133 is configured so that the radiation absorption rate thereof is greater than the radiation absorption rate of the portions 131 and 132, and radiation decays more readily at the portion 133 as compared to the portions 131 and 132. That is to say, the portion 131 is configured to maintain adhesion between the portion 131 and the sensor panel 110 while tolerating positional deviation of the sensor panel 110 in the planar direction. Also, the portion 132 is configured to maintain adhesion between the portion 132 and the sensor panel 120 while tolerating positional deviation of the sensor panel 120 in the planar direction. The portion 133 is configured with priority on absorption of part of the radiation X2 and deformation in the planar direction. For example, acrylic, urethane, and/or silicone resin is used for the portions 131 and 132, and metal of Au, Ag, Cu, Zn, Pb, Mg, Ti, W, Fe, Ni, Al, and/or Mo is used for the portion 133.

Note that it is sufficient for the portions 131 and 132 to have elasticity at ordinary temperature after having been formed. Ordinary temperature as used here means a temperature at which the apparatus 10 would normally be used, and generally means room temperature of an examination room (At least 0° C. or higher and 40° C. or lower. Typically around 25° C.). The portions 131 and 132 may further have adhesive force, to realize fixing to the respective sensor panels 110 and 120.

Figure 5B:
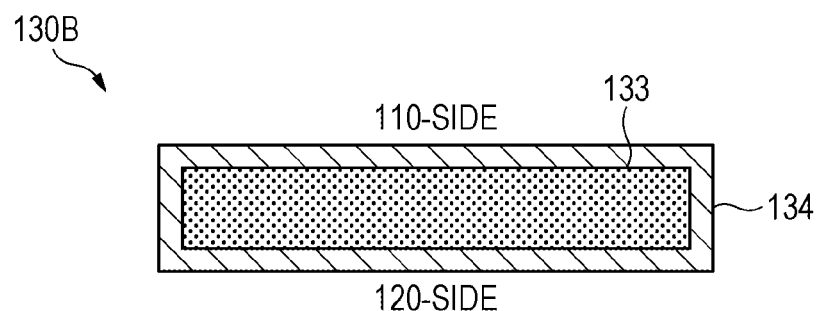
FIG. 5B is a diagram for describing a configuration example of an adhesion part.

FIG. 5B illustrates the configuration of the adhesion part 130B. This example differs from the adhesion part 130A in FIG. 5A, in that the sides of the portion 133 are further covered by a portion 134. It is sufficient for the same material as the portions 131 and 132 to be used for the portion 134, and the portion 134 can be configured to have greater elasticity than the portion 133.

Figure 5C:
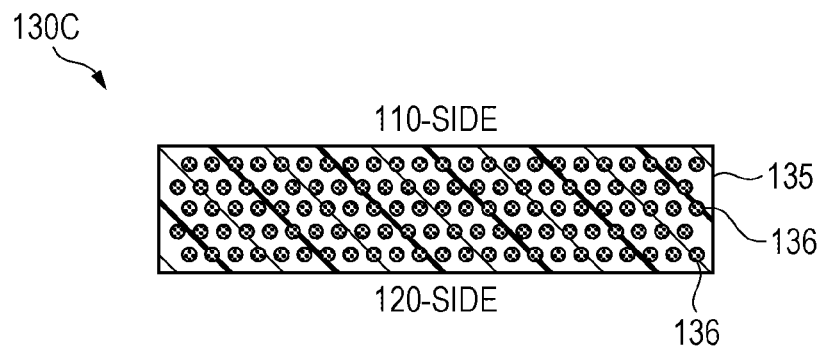
FIG. 5C is a diagram for describing a configuration example of an adhesion part.

FIG. 5C illustrates the configuration of the adhesion part 1300. The adhesion part 1300 has a member 135 having elasticity, and multiple metal particles 136 having radiation absorbency. The multiple metal particles 136 are contained within the member 135. Acrylic, urethane, and/or silicone resin is used for the member 135, and metal of Au, Ag, Cu, Zn, Pb, Mg, Ti, W, Fe, Ni, Al, and/or Mo is used for the metal particles 136. The metal particles 136 may be in powder form or spherical, and in the case of being spherical, the diameter (grain size) may be around 0.01 μm to 1 μm, for example.

When the distribution density of the multiple metal particles 136 is small in the member 135, the radiation absorption rate becomes small, and the elastic modulus becomes small (easily deformed). Also, when this distribution density is large, the radiation absorption rate becomes great, and the elastic modulus becomes great (not easily deformed). Accordingly, the multiple metal particles 136 are preferably distributed within the member 135 within a range of distribution density of 30% or more but 70% or less, for example.

As another example, an arrangement may be made where the distribution density of the metal particles 136 is small at portions closer to the sensor panel 110 or 120, and the distribution density is great at portions farther from the sensor panel 110 or 120. In conjunction with this, or instead of this, an arrangement may be made where the grain size of the metal particles 136 is small at portions closer to the sensor panel 110 or 120, and the grain size of the metal particles 136 is large at portions farther from the sensor panel 110 or 120.

Figure 5D:
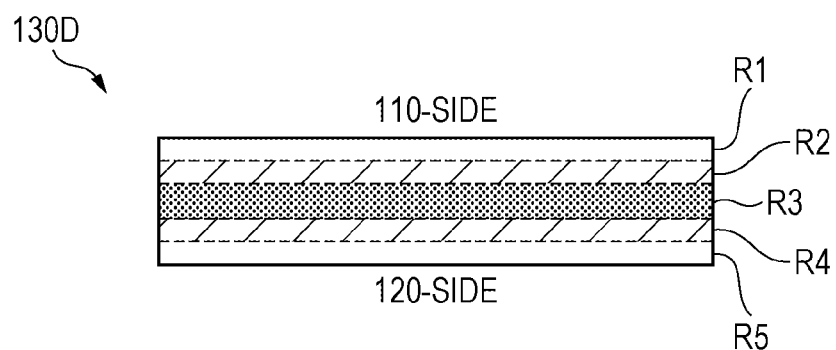
FIG. 5D is a diagram for describing a configuration example of an adhesion part.

FIG. 5D illustrates the configuration of the adhesion part 130D. The adhesion part 130D has regions R1, R2, R3, R4, and R5 in order from the sensor panel 110 side toward the sensor panel 120 side. Here, the elastic modulus of the regions R1, R2, R3, R4, and R5 respectively are $E_{R1}$, $E_{R2}$, $E_{R3}$, $E_{R4}$, and $E_{R5}$, and the radiation absorption rate of the regions R1, R2, R3, R4, and R5 respectively are $A_{R1}$, $A_{R2}$, $A_{E3}$, $A_{R4}$, and $A_{R5}$. At this time, $E_{R1}<E_{R2}<E_{R3}$ and $E_{R5}<E_{R4}<E_{R3}$ hold, and $A_{R1}<A_{R2}<A_{R3}$, and $A_{R5}<A_{R4}<A_{R3}$ hold. These regions R1 through R5 can also be realized by the configuration exemplified with reference to FIG. 5C.

Although five regions R1 through R5 have been exemplified in the example in FIG. 5D, the number of regions is not restricted to this example, and alternatively, the adhesion part 130D may be configured with the elasticity and radiation absorbency changing gradually (gently instead of being stepped).

As yet another example, the elasticity of the adhesion part 130 may change in the planar direction of the sensor panel 110. For example, the adhesion part 130 may be configured having a middle portion and a peripheral portion thereof in the planar direction of the sensor panel 110, with the elastic modulus of the middle portion being smaller than the elastic modulus of the peripheral portion. In this case, the peripheral portion may be stipulated as being a portion on the outer side of the outer edge of the protective film 114 in planar view.

The adhesion part 130 has tolerance regarding relative positional change of the sensor panels 110 and 120 in the planar direction due to the configuration exemplified in FIGS. 5A through 5D, but when this tolerance amount is set unnecessarily high, the following problem can occur. That is to say, there is a possibility that the relative position between the sensor panels 110 and 120 may change due to slight vibrations from the subject 40 changing positions or the like, while shooting. Normally (in a state with substantially no vibrations), the multiple radiation detecting elements on the sensor panel 110 are each situated generally directly above the multiple radiation detecting elements of the sensor panel 120. Accordingly, the multiple signals making up the image data from the sensor panel 110 corresponds to each of the multiple signals making up image data from the sensor panel 120, so energy subtraction processing can be appropriately be performed on these two sets of image data. However, if the relative positions of the sensor panels 110 and 120 change due to the above slight vibrations, these correlations no longer hold, and the energy subtraction processing cannot be appropriately performed.

Accordingly, a predetermined upper limit value is preferably set for the amount of tolerance regarding change in relative position of the sensor panels 110 and 120 in the planar direction. This upper limit value is preferably set to be smaller than the pitch of array of the multiple radiation detecting elements in the sensor array 112 (or 122), for example. This upper limit value may be set taking into consideration, for example, vibrations occurring at the time of loading the radiological imaging apparatus 10 onto a wagon or the like or carrying to transport. For example, with the pitch of the array of the multiple radiation detecting elements as P, the relation of $L_{SHIFT}<P$ preferably holds regarding the distance $L_{sHIFT}$ exemplified with reference to FIG. 4B. The same is true for the thickness of the adhesion part 130.

In order to realize this, the adhesion part 130 preferably has elastic modulus of 1 MPa or greater but 40 MPa or smaller under temperature conditions of 0° C. or higher and 40° C. or lower (testing method; ISO527-1 (JIS K7161)), for example.

In the manufacturing process of the radiological imaging apparatus 10, the adhesion part 130 is obtained by mixing a material having elasticity and a material having radiation absorbency at a predetermined ratio. For example, this mixed material may be coated on the sensor panel 110, following which the sensor panel 120 is adhered to the sensor panel 110. This coating may be performed by a known method, such as spin coating, laminating, and so forth. In another example, two or more materials having elastic moduli and radiation absorption rates different from each other may be prepared, and those corresponding to the parts of the adhesion part 130 being coated in order for formation thereof. These materials may each be obtained by changing the mixture ratio of material having elasticity and material having radiation absorbency. In this case, the above mixture ratio is changed in accordance with the part of the adhesion part 130 being formed, so the coating may be performed using two or more sprays and changing the amount of spray.

Figure 6A:
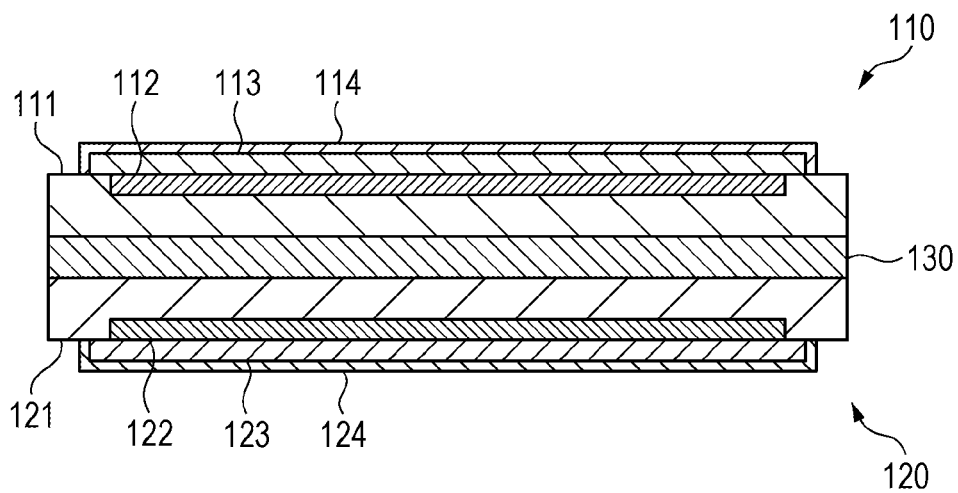
FIG. 6A is a diagram for describing several examples of structures where two sensor panels are bonded to each other.
Figure 6B:
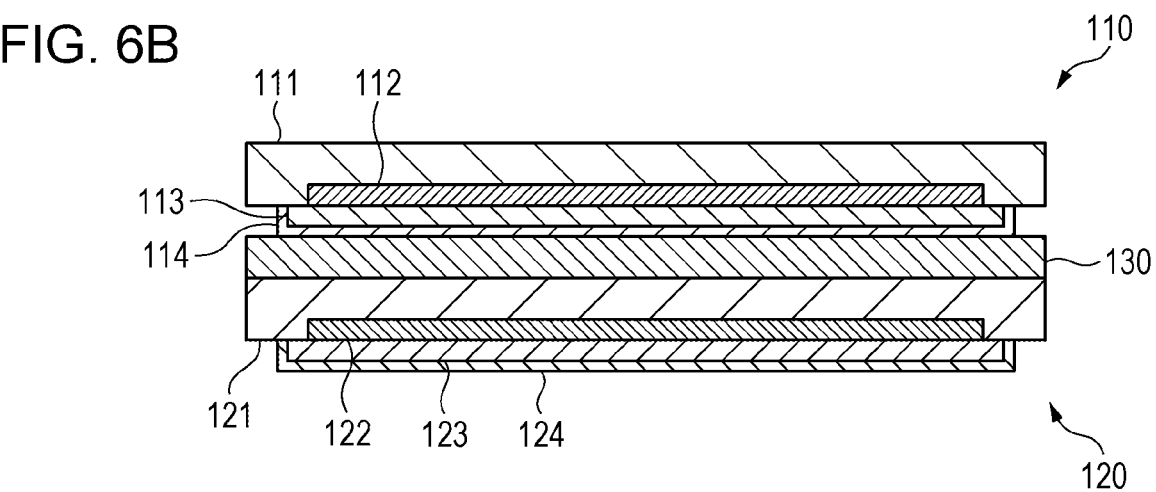
FIG. 6B is a diagram for describing several examples of structures where two sensor panels are bonded to each other.
Figure 6C:
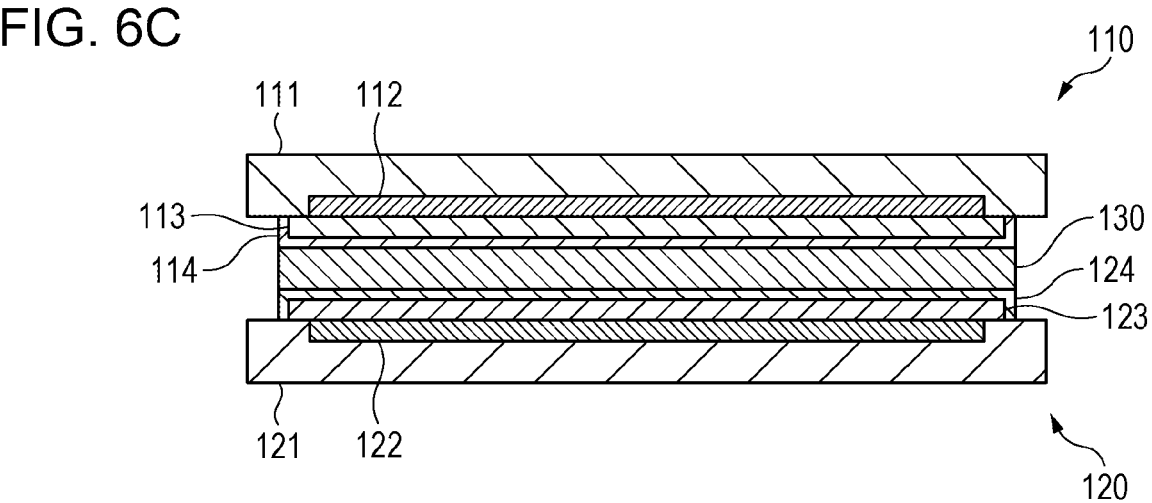
FIG. 6C is a diagram for describing several examples of structures where two sensor panels are bonded to each other.

FIGS. 6A through 6C illustrate other forms of adhesion of the sensor panels 110 and 120 by the adhesion part 130, in the same way as in FIG. 4A.

In the example in FIG. 6A, the sensor panels 110 and 120 are adhered to each other by the adhesion part 130 so that the sensor panel 110 has a front-side irradiation configuration and the sensor panel 120 has a back-side irradiation configuration. Specifically, the substrate 111 and substrate 121 are positioned between the scintillator 113 and scintillator 123, and the adhesion part 130 adheres the lower face of the substrate 111 and the lower face of the substrate 121 to each other.

In the example in FIG. 6B, the sensor panels 110 and 120 are adhered to each other by the adhesion part 130 so that both have back-side irradiation configurations. Specifically, the scintillator 113 and substrate 121 are positioned between the substrate 111 and the scintillator 123, and the adhesion part 130 adheres the upper face of the protective film 114 and the lower face of the substrate 121 to each other.

In the example in FIG. 6C, the sensor panels 110 and 120 are adhered to each other by the adhesion part 130 so that the sensor panel 110 has a back-side irradiation configuration and the sensor panel 120 has a front-side irradiation configuration. Specifically, the scintillator 113 and scintillator 123 are positioned between the substrates 111 and 121, and the adhesion part 130 adheres the upper face of the protective film 114 and the upper face of the protective film 124 to each other.

Although omitted from illustration here, a cushioning material may be disposed between an upper portion (plate member at the subject 40 side) of the housing of the radiological imaging apparatus 10 and the sensor panel 110, to mitigate shock from the subject 40 being positioned or lying down. In this case, the adhesion part 130 may be configured having a greater elastic modulus than the elastic modulus of the cushioning material, and having a greater radiation absorption rate than the radiation absorption rate of the cushioning material.

Although several preferable forms have been exemplified, the present invention is not restricted to these examples, and partial changes may be made without departing from the essence of the present invention. Various terms used in the present specification have only been used to describe the present invention and it goes without saying that the present invention is not to be restricted to the strict meaning of these terms, and equivalencies may be included.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiological imaging apparatus, comprising:
   a first panel where a plurality of radiation detecting elements are arrayed on a first substrate;
   a second panel where a plurality of radiation detecting elements are arrayed on a second substrate; and
   a sheet-shaped adhesion part configured to adhere a second-panel side face of the first panel and a first-panel side face of the second panel to each other, so that the first panel and the second panel are overlaid on each other in planar view as to an upper face of the first substrate,
   wherein the adhesion part has radiation absorbency,
   wherein the adhesion part is configured so that change in relative positions of the first panel and the second panel in a planar direction parallel to the upper face of the first substrate is smaller than a pitch of array of the radiation detecting elements, and adhesion of the first panel and the second panel is maintained,
   wherein the adhesion part includes
       a first portion that is a part of the adhesion part and is located on a side of the first panel in the adhesion part,
       a second portion that is a part of the adhesion part and is located on a side of the second panel in the adhesion part, and
       a third portion that is a part of the adhesion part and is located between the first portion and the second portion,
   and wherein a radiation absorption rate of the third portion is greater than a radiation absorption rate of the first portion and the radiation absorption rate of the third portion is greater than a radiation absorption rate of the second portion.

2. The radiological imaging apparatus according to claim 1,
   wherein the adhesion part includes a portion having radiation absorbency and elasticity.

3. The radiological imaging apparatus according to claim 2,
   wherein the adhesion part includes
       a first member having elasticity, and
       a second member contained within the first member and having radiation absorbency.

4. The radiological imaging apparatus according to claim 3,
   wherein the second member includes metal particles, and a plurality of the metal particles are contained within the first member.

5. The radiological imaging apparatus according to claim 4,
   wherein a distribution density of the plurality of metal particles in the first member is 30% or more but 70% or less.

6. The radiological imaging apparatus according to claim 3,
   wherein the first member includes an acrylic, urethane, and/or silicone resin,
   and wherein the second member includes a metal of Au, Ag, Cu, Zn, Pb, Mg, Ti, W, Fe, Ni, Al, and/or Mo.

7. The radiological imaging apparatus according to claim 1,
   wherein the adhesion part has an elastic modulus of 1 MPa or greater but 40 MPa or smaller under temperature conditions of 0° C. or higher and 40° C. or lower.

8. The radiological imaging apparatus according to claim 1,
   wherein the first panel further has a first scintillator disposed on the first substrate, covering the plurality of radiation detecting elements,
   wherein the second panel further has a second scintillator disposed on the second substrate, covering the plurality of radiation detecting elements,
   wherein the first panel is disposed above the second panel,
   and wherein the adhesion part adheres the first panel and the second panel, satisfying one of
       the first substrate and the second scintillator being interposed between the first scintillator and the second substrate,
       the first substrate and the second substrate being interposed between the first scintillator and the second scintillator,
       the first scintillator and the second substrate being interposed between first substrate and the second scintillator, and
       the first scintillator and the second scintillator being disposed between the first substrate and the second substrate.

9. An imaging system comprising: the radiological imaging apparatus according to claim 1; and a processor configured to process signals from the radiological imaging apparatus.

10. The radiological imaging apparatus according to claim 1,
    wherein the sheet-shaped adhesion part abuts and adheres to the second-panel side face of the first panel, and the sheet-shaped adhesion part abuts and adheres to the first-panel side face of the second panel.

11. The radiological imaging apparatus according to claim 1,
    wherein an elastic modulus of the first portion is smaller than an elastic modulus of the third portion and an elastic modulus of the second portion is smaller than the elastic modulus of the third portion.

12. The radiological imaging apparatus according to claim 11,
    wherein the first portion and the second portion have adhesive force.

13. The radiological imaging apparatus according to claim 11, wherein the adhesion part further includes a fourth portion that connects the first portion and the second portion while covering a side face of the third portion, and an elastic modulus of the fourth portion is smaller than the elastic modulus of the third portion.

14. The radiological imaging apparatus according to claim 11,
wherein the first portion and the second portion include an acrylic, urethane, and/or silicone resin,
and wherein the third portion includes a metal of Au, Ag, Cu, Zn, Pb, Mg, Ti, W, Fe, Ni, Al, and/or Mo.

15. A manufacturing method of a radiological imaging apparatus, the method comprising:
a process of preparing each of a first panel where a plurality of radiation detecting elements are arrayed on a first substrate, and a second panel where a plurality of radiation detecting elements are arrayed on a second substrate; and
a process of adhering a second-panel side face of the first panel and a first-panel side face of the second panel to each other by a sheet-shaped adhesion part which has radiation absorbency, so that the first panel and the second panel are overlaid on each other in planar view as to an upper face of the first substrate,
wherein the adhesion part is configured so that change in relative positions of the first panel and the second panel in a planar direction parallel to the upper face of the first substrate is smaller than a pitch of array of the radiation detecting elements, and adhesion of the first panel and the second panel is maintained,
wherein the adhesion part includes
a first portion that is a part of the adhesion part and is located on a side of the first panel in the adhesion part,
a second portion that is a part of the adhesion part and is located on a side of the second panel in the adhesion part, and
a third portion that is a part of the adhesion part and is located between the first portion and the second portion,
and wherein a radiation absorption rate of the third portion is greater than a radiation absorption rate of the first portion and the radiation absorption rate of the third portion is greater than a radiation absorption rate of the second portion.

16. The manufacturing method of a radiological imaging apparatus according to claim 15,
wherein, in the process of adhering, the first panel is coated by a member where a first material having elasticity and a second material having radiation absorbency have been mixed, and thereafter the second panel is adhered to the first panel.

17. The manufacturing method of a radiological imaging apparatus according to claim 15,
wherein, in the process of adhering, the first panel is coated by a first material having elasticity by spraying while being coated by a second material having radiation absorbency by spraying, and thereafter the second panel is adhered to the first panel.

18. A radiological imaging apparatus, comprising:
a first panel where a plurality of radiation detecting elements are arrayed on a first substrate;
a second panel where a plurality of radiation detecting elements are arrayed on a second substrate; and
a sheet-shaped adhesion part configured to adhere a second-panel side face of the first panel and a first-panel side face of the second panel to each other, so that the first panel and the second panel are overlaid on each other in planar view as to an upper face of the first substrate,
wherein the adhesion part includes
a first portion that is a part of the adhesion part and is located on a side of the first panel in the adhesion part,
a second portion that is a part of the adhesion part and is located on a side of the second panel in the adhesion part, and
a third portion that is a part of the adhesion part and is located between the first portion and the second portion,
and wherein a radiation absorption rate of the third portion is greater than a radiation absorption rate of the first portion and the radiation absorption rate of the third portion is greater than a radiation absorption rate of the second portion.

19. A radiological imaging apparatus, comprising:
a first panel where a plurality of radiation detecting elements are arrayed on a first substrate;
a second panel where a plurality of radiation detecting elements are arrayed on a second substrate; and
a sheet-shaped adhesion part configured to adhere a second-panel side face of the first panel and a first-panel side face of the second panel to each other, so that the first panel and the second panel are overlaid on each other in planar view as to an upper face of the first substrate,
wherein the adhesion part includes
a first portion that is a part of the adhesion part and is located on a side of the first panel in the adhesion part,
a second portion that is a part of the adhesion part and is located on a side of the second panel in the adhesion part, and
a third portion that is a part of the adhesion part and is located between the first portion and the second portion,
and wherein an elastic modulus of the first portion is smaller than an elastic modulus of the third portion and an elastic modulus of the second portion is smaller than the elastic modulus of the third portion.

* * * * *